United States Patent [19]

Hayward et al.

[11] 4,319,566

[45] Mar. 16, 1982

[54] METHOD AND APPARATUS FOR INHALATION REWARMING

[76] Inventors: John Hayward, 570 Linnet La., Victoria, B.C., Canada, V8X 3X1; Robert Douwens, 2924 Shelbourne St., Victoria, B.C., Canada, V8R 4M6

[21] Appl. No.: 170,536

[22] Filed: Jul. 21, 1980

[51] Int. Cl.³ .............................................. A61M 16/00
[52] U.S. Cl. ........................... 128/203.26; 128/203.12; 128/203.16; 128/203.25; 128/204.17
[58] Field of Search ..................... 128/203.16, 203.17, 128/203.25, 203.26, 203.27, 203.29, 204.17, 203.12, 203.14, 205.24, 205.25, 200.14, 200.15, 200.16, 200.17, 200.18, 200.19, 200.21, 200.22, 200.23, 203.29, 205.18, 205.11, 203.28; 122/13 A, 13 R, 17, 16, 39, 40, 247; 219/273, 275, 276, 271, 304; 261/DIG. 65

[56] References Cited

U.S. PATENT DOCUMENTS

| | | | |
|---|---|---|---|
| 433,442 | 8/1890 | Bossler et al. | 122/247 |
| 533,127 | 1/1895 | Horton | 128/203.29 |
| 631,575 | 8/1899 | Koch | 128/203.16 |
| 955,121 | 4/1910 | Hollett | 128/203.25 |
| 1,784,695 | 12/1930 | Lang | 219/304 |
| 2,023,324 | 12/1935 | Johnson et al. | 128/203.17 |
| 2,116,328 | 5/1938 | Silten | 128/203.16 |
| 3,326,214 | 6/1967 | McCoy | 128/212 |
| 3,434,471 | 3/1969 | Liston | 128/145.8 |
| 3,506,003 | 4/1970 | Gregory | 128/192 |
| 3,526,222 | 2/1971 | Gauthier | 128/212 |
| 3,565,072 | 8/1971 | Peters et al. | 128/145.5 |
| 3,598,116 | 8/1981 | Bird | 128/145.8 |
| 3,630,196 | 12/1971 | Bird et al. | 128/145.8 |
| 3,638,926 | 2/1972 | Melville et al. | 261/130 |
| 3,659,604 | 5/1972 | Melville et al. | 128/212 |
| 3,664,337 | 5/1972 | Lindsey et al. | 128/194 |
| 3,771,721 | 11/1978 | Amerongen | 239/338 |
| 3,820,540 | 6/1974 | Hirtz et al. | 128/212 |
| 3,871,373 | 3/1975 | Jackson | 128/193 |
| 3,902,488 | 9/1975 | Sheppard | 128/212 |
| 3,903,883 | 9/1975 | Pecina et al. | 128/193 |
| 3,912,795 | 10/1975 | Jackson | 128/36 R |
| 3,974,830 | 8/1976 | LaVerre | 128/212 |
| 4,007,238 | 2/1977 | Glenn | 128/78 A |
| 4,009,713 | 3/1977 | Simmons et al. | 128/193 |
| 4,016,878 | 4/1977 | Castel et al. | 128/212 |
| 4,019,511 | 4/1977 | Choporis et al. | 128/212 |
| 4,026,285 | 5/1977 | Jackson | 128/192 |
| 4,028,445 | 6/1977 | Hickmann et al. | 261/142 |
| 4,038,980 | 8/1977 | Fodor | 128/193 |
| 4,051,205 | 9/1977 | Grant | 261/70 |
| 4,060,576 | 11/1977 | Grant | 261/130 |
| 4,084,587 | 4/1978 | Lindsey | 128/193 |
| 4,101,611 | 7/1978 | Williams | 261/142 |
| 4,121,583 | 10/1978 | Chen | 128/192 |
| 4,165,738 | 8/1979 | Graves et al. | 128/205.25 |
| 4,200,093 | 4/1980 | Camp | 128/203.16 |

FOREIGN PATENT DOCUMENTS

| | | | |
|---|---|---|---|
| 9928 | of 1903 | United Kingdom | 128/203.16 |
| 2012 | of 1910 | United Kingdom | 128/203.25 |
| 421708 | 10/1934 | United Kingdom | 128/203.17 |

*Primary Examiner*—Henry J. Recla

[57] ABSTRACT

Apparatus is provided herein for inhalation rewarming for the treatment of victims of hypothermia. The apparatus includes a water reservoir. A steam chamber communicates with ambient air. A heater means is associated with such water chamber, for the generation of steam into such steam chamber. An opening is provided admitting air to the steam chamber, thereby to provide an air-steam mixture. A first conductor is connected to the steam chamber for the conducting of the air-steam mixture from the steam chamber in a first direction. A valve is provided in the first conductor for varying the inflow of the ambient air while simultaneously reciprocally varying the inflow of the air-steam mixture and providing a substantially constant volume flow into the first conduit means. The valve includes actuated operator means for initially introducing sufficient ambient air into the air-steam mixture in the first conductor means to provide a continuous flow of the water-saturated air at the temperature of about 35° C.–about 45° C. A flexible conduit leads from the valve means for conducting the water-saturated air in the first direction. Finally a breathing mask is connected to the flexible conduit means downstream of the valve means. The breathing mask includes one-way valves therein to permit the water-saturated air to flow only in the first direction to the breathing mask, whereby the water-saturated air at the temperature of about 35° C.–about 45° C. is drawn into the breathing mask by the negative pressure produced by human inhalation, and exhaled air produced by human inhalation is vented. Thus, a simple, effective apparatus for inhalation rewarming has been provided which has special relevance to first-aid treatment of accidental hypothermia.

28 Claims, 6 Drawing Figures

METHOD AND APPARATUS FOR INHALATION REWARMING

BACKGROUND OF THE INVENTION

1. Field of the Invention

This invention relates to a method and apparatus for the rewarming of hypothermic humans.

2. Description of the Prior Art

In the profoundly hypothermic human, the lowered ventilation rate causes less heat donation by the inhalation method and provides "stabilization" of core temperature during transport to hospital. In mild or moderate hypothermia, actual "rewarming" of the victim is desirable. In such victims, ventilation rate is elevated and a satisfactory rewarming rate of the critical core is obtained. Victims who are hypothermic and lack vital signs (e.g., cold water near-drowning) should not be rewarmed until arrival at the hospital. Inhalation therapy based on the spontaneous ventilation of the victim ensures that this will be the case.

Accidental hypothermia is a common hazard to man's endeavours in cold air and water environments. Because of the potential for rapid heat loss in cold water immersion and in mountain accidents, accidental hypothermia often becomes a true medical emergency with substantial mortality. Yet, despite the long-standing recognition of this problem, a single definitive plan for first-aid therapy of accidental hypothermia has not been accepted. Because hypothermia fatalities occasionally occur even after removal of the victim from his cold environment, organizations involved in the recovery of hypothermia victims should have the capacity to give effective emergency medical treatment.

A traditional way of treatment of accidental hypothermia has been rapid peripheral rewarming. This has been effective even in the profoundly hypothermic victim. However, the peripheral vasodilation which usually accompanies most forms of external rewarming may precipitate the well-described "afterdrop" in core body temperature, which can potentiate the possibility of ventricular fibrillation from further cooling of the myocardium. The peripheral vasodilation accompanying rapid external rewarming may also produce "rewarming shock", a form of hypovolemia secondary to diminished central blood volume. This latter effect is particularly evident in hypothermia of slow onset, where intravascular volume is decreased secondary to fluid shifts. Hence, rapid peripheral rewarming of the accidental hypothermia victim is attended by a number of potential hazards which cannot be well managed in the non-hospital setting.

It is now established that the most effective and safe method for rewarming of severely hypothermic humans is by donation of heat directly to the core of the body rather than via the periphery. Accordingly, hospital management of such victims most frequently involves peritoneal dialysis (warm saline in the abdominal cavity) and inhalation (or airway) rewarming. Of these two methods, only inhalation rewarming is suitable for use by non-medical personnel at the rescue site or during transport to hospital. Inhalation of warm (about 42°–45° C.), water-saturated air or oxygen donates heat directly to the head, neck and thoracic core (the critical core). Although the amount of heat donated by this method is not large, its transfer to the most important tissues of the body is strategic, and results in minimum "afterdrop" of core temperature and does not stimulate return of peripheral blood with possible elevations of acidity and potassium concentration.

Methods of inhalation rewarming are now used routinely in hospitals and an electrically powered inhalation rewarming unit has been developed for the field. However, electricity is not always available in remote regions where hypothermic victims are found. Also, such units have the disadvantage of requiring a source of compressed gas (e.g., oxygen).

Some reports of inhalation rewarming techniques are by M. L. Collis et al "Accidental Hypothermia: An Experimental Study of Practical Rewarming Methods" Aviation, Space, And Environment Medicine, July 1977, p. 625; and by E. L. L. Lloyd "Accidental Hypothermia Treated by Central Rewarming Through the Airway", Brit. J. Anaeth. (1973) 45, p. 41.

The patent literature is replete with devices that pertain to warming and humidifying air or anaesthesia gases. Among these patents are the following U.S. Pat. Nos.:

| | | | | |
|---|---|---|---|---|
| 3,434,471 | 3,506,003 | 3,526,222 | 3,638,926 | 3,659,604 |
| 3,820,540 | 3,871,373 | 3,902,883 | 3,974,830 | 3,912,795 |
| 3,771,721 | Re. 30046 | 3,664,337 | 3,630,196 | 3,598,116 |
| 3,326,214 | 3,565,072 | 3,902,488 | 4,028,445 | 4,038,980 |
| 4,051,205 | 4,060,576 | 4,121,583 | 4,016,878 | 4,019,511 |
| 4,026,285 | 4,007,238 | 4,009,713 | 4,084,587 | 4,101,611 |

SUMMARY OF THE INVENTION

(i) Aims of the Invention

Nevertheless, the provision of a practical apparatus for inhalation rewarming has not been taught. Accordingly, one object of this invention is the provision of a small, compact, light-weight apparatus which may be heated by means of a gas, e.g., propane, or by electricity, e.g., 110 V or 12 V of low wattage.

Another object of this invention is the provision of such an apparatus which is simple in operation and may be effectively and safely administered by non-medical personnel with minimal training.

A further object of this invention is the provision of such an apparatus which has a rapid warm-up so that steam may be available within 10 seconds of startup.

Yet another object of this invention is the provision of such an apparatus incorporation a temperature regulating system.

A still further object of this invention is the provision of such an apparatus in which there is no requirement for compressed sources of breathing gases, (e.g., air or $O_2$), since normal breathing of the victim should provide transport of the warm, water-saturated air.

Yet a further object of this invention is the provision of such an apparatus which provides efficient operation in extreme cold environments through the use of exhaust gases for additional heating of the water reservoir and for the maintenance of the steam chamber temperature directly and by preheating of cold, ambient, intake air.

Still a further object of this invention is the provision of such an apparatus having a high capacity steam production so that it may potentiate multiple-victim treatment simultaneously.

Yet a further object of this invention is the provision of such an apparatus having an accessory function which makes it usable as a "stove" for heating food, drinks, and melting snow as a water source.

Another object of this invention is to provide a novel method for inhalation rewarming.

(ii) Statements of Invention

This invention, therefore, provides apparatus for inhalation rewarming for the treatment of victims of hypothermia, the apparatus comprising: (a) a water reservoir; (b) a steam chamber communicating with ambient air; (c) a heater means, associated with such water chamber for the generation of steam into such steam chamber; (d) means for admitting air to the steam chamber, thereby to provide an air-steam mixture; (e) first conductor means connected to the steam chamber for the conducting of the air-steam mixture from the steam chamber in a first direction; (f) valve means in the first conductor means for varying the inflow of the ambient air while simultaneously reciprocally varying the inflow of the air-steam mixture and providing a substantially constant volume flow into the first conduit means, the valve means including actuated operator means for initially introducing sufficient ambient air into the air-steam mixture in the first conductor means to provide a continuous flow of the water-saturated air at the temperature of about 35° C.–about 45° C.; (g) flexible conduit means leading from the valve means for conducting the water-saturated air in the first direction; and (h) a breathing mask connected to the flexible conduit means downstream of the valve means, the breathing mask including one-way valves therein to permit the water-saturated air to flow only in the first direction to the breathing mask, whereby the water-saturated air at a temperature of about 35° C.–about 45° C. is drawn into the breathing mask by the negative pressure produced by human inhalation, and exhaled air produced by human inhalation is vented.

This invention also provides apparatus for inhalation rewarming for the treatment of victims of hypothermia comprising: (a) a water reservoir; (b) a steam chamber communicating with ambient air; (c) a heater means, associated with such water chamber, for the generation of steam into the steam chamber; (d) means for admitting air at ambient pressure to the steam chamber, thereby to provide an air-steam mixture; (e) first conductor means connected to the steam chamber for the conducting of the air-steam mixture at ambient pressure from the steam chamber in a first direction; (f) valve means in the first conductor means for varying the inflow of the ambient air while simultaneously reciprocally varying the inflow of the air-steam mixture and providing a substantially constant volume flow into the first conduit means, the valve means including actuated operator means for initially introducing sufficient ambient air into the airsteam mixture in the first conductor means to provide a continuous flow of water-saturated air at a temperature of about 35° C.–about 45° C. and for maintaining the continuous flow of the water-saturated air at such temperature of about 35° C.–about 45° C.; (g) flexible conduit means leading from the valve means for conducting the water-saturated air in the first direction; and (h) a breathing mask connected to the flexible conduit means downstream of the valve means, the breathing mask including one-way valves therein to permit the water-saturated air to flow only in the first direction to the breathing mask, whereby the water-saturated air at such temperature of about 35° C.–about 45° C. is drawn into the breathing mask by the negative pressure produced by human inhalation, and exhaled air produced by human inhalation is vented.

This invention also provides apparatus for inhalation rewarming for the treatment of victims of hypothermia, comprising: (a) first conductor means for connection to a source of an air-steam mixture for conducting the air-steam mixture in a first direction; (b) valve means in the first conductor means for varying the inflow of the ambient air while simultaneously reciprocally varying the inflow of the air-steam mixture and providing a substantially constant volume flow into the first conduit means, the valve means including actuated operator means for initially introducing sufficient ambient air into the air-steam mixture in the first conductor means to provide a substantially continuous flow of water-saturated air at a temperature of about 35° C.–about 45° C.; (c) flexible conduit means leading from the valve means for conducting the water-saturated air in the first direction; and (d) a breathing mask connected to the flexible conduit means downstream of the valve means, the breathing mask including one-way valves therein to permit the water-saturated air flow only in the first direction to the breathing mask, whereby the water-saturated air at such temperature of about 35° C.–about 45° C. is drawn into the breathing mask by the negative pressure produced by human inhalation, and exhaled air produced by human inhalation is vented.

As well, the invention provides a valve, for use in an apparatus for inhalation rewarming, the valve being specially designed for introducing sufficient ambient air into an air-steam mixture flowing in a conduit to provide water-saturated air at a preselected temperature of about 35° C.–about 45° C., and for maintaining the continuous flow of such water-saturated air at such temperature of about 35° C.–about 45° C. by actuated operator means for varying the inflow of the ambient air while simultaneously reciprocally varying the inflow of the incoming airsteam mixture, the valve comprising: (a) a hollow, tubular closed-ended inner body having an axial flow passage and a single arcuate opening thereinto; (b) an outer coaxial, open-ended, hollow tubular body having an axial flow passage and a pair of discontinuous arcuate orifices thereinto, the outer tubular body being disposed concentrically and relatively rotatably around the inner body; (c) a hollow connecting the connected at right angles to the outer body, the connecting tube having an axial flow passage; (d) an inlet for an air-steam mixture to the valve means through the connecting tube and into one such discontinuous arcuate orifice; (e) an inlet for ambient air to the valve means, through the arcuate opening in the hollow inner body and into the other one of the discontinuous arcuate orifices; and (f) means for rotating the inner tubular body with respect to the outer tubular body to change the overlapping areas of the arcuate opening in the inner tubular body and the arcuate openings in the outer tubular body, thereby to allow a varying input of the ambient air and a reciprocal varying input of the air-steam mixture in proportions to result in temperature control of the effluent, water-saturated air while maintaining a substantially constant flow of the water-saturated air.

This invention also provides a valve for use in an apparatus for inhalation rewarming for the treatment of victims of hypothermia, the valve being specially designed for introducing sufficient ambient air into an air-steam mixture flowing in a conduit to provide water-saturated air at a preselected suitable temperature and for maintaining the continuous flow of the water-saturated air at a temperature of about 35° C.–about 45°

C. by actuated operator means for varying the inflow of the ambient air while simultaneously reciprocally varying the inflow of the incoming air-steam mixture, the valve comprising: (i) an inner capped hollow body member having an axial flow passage, and a control orifice associated therewith; (ii) an outer hollow body member having an axial flow passage disposed concentrically and in a vertical orientation relatively rotatable to the inner body member, the outer body member having a plurality of orifices, associated with the central orifice and a plurality of outlet conduits leading therefrom; (iii) an inlet for an air-steam mixture to enter the inner body member; (iv) an inlet for ambient air to the inner body member; and (v) means for rotating the inner tubular body with respect to the outer tubular body to change the overlapping areas of the arcuate opening in the inner tubular body and the arcuate openings in the outer tubular body, thereby to allow a varying input of the ambient air and a reciprocal varying input of the air-steam mixture in proportions to result in temperature control of the effluent, water-saturated air while maintaining a constant flow of the water-saturated air.

This invention also provides a method for the treatment of a human suffering from hypothermia which comprises the steps of: (1) providing or generating an air-steam mixture; (2) converting the air-steam mixture to water-saturated air at a temperature of about 35° C.–about 45° C. by the addition of controlled amounts of ambient air to the air-steam mixture while substantially simultaneously condensing water out of the air-steam mixture; (3) maintaining a substantially constant flow of the water-saturated air at a temperature of about 35° C.–about 45° C. by varying the volume of ambient air while simultaneously reciprocally varying the volume of the air-steam mixture; and (4) arranging for the human to inhale the water-saturated air at that temperature of about 35° C.–about 45° C. by spontaneous human ventilation.

(iii) Other Features of the Invention

By a feature of the invention, the temperature is 42°–45° C.

By a further feature of the invention, the apparatus includes (i) second conductor means leading from the valve means, the second conductor means including a water trap therein for collecting water condensed out of the air-steam mixture in providing the water-saturated air at the temperature of about 35° C.–about 45° C.

By a further feature of the invention, the heater means comprises a suitable gas, e.g. propane gas heated hollow cone surrounded by an annular water reservoir.

By a further feature of the invention, the heater means comprises an electrically heated hollow cylinder surrounded by an annular water reservoir.

By a further feature of the invention, the apparatus includes a coil traversing the heated hollow core and leading from the bottom of the water reservoir to the bottom of the steam chamber, whereby heat is conducted to the water via the water-filled coil.

By a further feature of the invention, the steam chamber is disposed atop the annular water reservoir in open communication therewith.

By a further feature of the invention, the apparatus includes means for preheating the air entering the steam chamber by exhaust heat from the heater means.

By a further feature of the invention, the valve means is manually operable.

By a further feature of the invention, the valve includes a plurality of outlet means leading to a similar plurality of second flexible conduit means, each leading to an associated breathing mask.

By a further feature of the invention, the apparatus includes a control means to limit the maximum temperature of the water-saturated air the control means comprising sensing means, adjacent to the breathing mask, to sense a predetermined maximum temperature of the water-saturated air, and non-manual valve operator means, actuated by the sensing means, to increase the input of ambient air to the valve means, while simultaneously reciprocally reducing the input of the air-steam mixture until the maximum temperature of the water-saturated air is reduced while the volume of flow of the water-saturated air is maintained.

By a further feature of the invention, upon sensing of the maximum temperature of the water-saturated air, means are activated to provide blocking of the steam source to the valve until the maximum temperature is reduced.

By a further feature of the invention, upon sensing of the maximum temperature of the water-saturated air, means are activated to provide increased input of ambient air until the maximum temperature is reduced.

(iv) Brief Description of One Embodiment of the Invention

Thus, in one embodiment of this invention, the portable rewarming device consists of a breathing mask attached to a one-way air flow system. Temperature of the water-saturated air breathed by the patient is monitored by a dial thermometer. Water-saturated air is transported to the one-way air flow system and mask by a flexible hose attached to a temperature-regulating valve via a water-trap for condensed water vapour. This manually-controlled valve mixes ambient air and an air-steam mixture at ambient pressure from the steam generator to provide water-saturated air of the desired temperature (e.g., 43° C.). A constant flow potential is provided by this valve for all possible control positions. The steam generator is heated by propane from an adjacent cylinder via shutoff and fine control valves. Heat given off by the generator is directed around the propane tank by a shroud to ensure vaporization of the propane in extremely cold environments.

An opening is provided in the generator for lighting the burner. Another opening is provided for adding water to the generator. A transparent gauge is provided for indicating water level. Two adjustable stabilizers, and a carrying handle, are also provided. Ambient air (at ambient pressure) enters the steam chamber via channels in the upper part of the generator, which results in preheating of entering air due to the high temperature of the metal exposed to the exhaust gases. This maintains the high temperature of the air-steam mixture despite cold ambient air supply.

Although the temperature regulating valve is designed for simple and effective operation, it is possible that operator error could cause excessive temperature of the inhalate water-saturated air. As a safety feature, an electronic control may be provided which operates as a high-temperature alarm and limiting device. An electronic temperature sensor, e.g., a semiconductor, is located in the flexible hose, near the one-way air flow system.

When the temperature of the water-saturated air exceeds 45° C. (or a setting near this, according to choice), the opening allows cool ambient air into the air passage. This opening is provided by a solenoid valve activated by a removable connector from a rechargeable, battery-operated, control box. During activation of this limiting device, audible and visible alarms signal the need for manual adjustment of the temperature-regulating valve. If such adjustment is delayed, the electronic valve will provide control of inhalate temperature within a satisfactory range by intermittent activation. A button permits pre-testing of the function of this accessory device.

The steam generating capacity of the propane-fired apparatus is sufficient to provide an air-steam mixture which can be converted to water-saturated air at 43° C. to three hypothermic patients at one time. A modified temperature-control valve, based on the operational principle described earlier, is used for this mode.

BRIEF DESCRIPTION OF THE DRAWINGS

In the accompanying drawings.

DESCRIPTION OF PREFERRED EMBODIMENTS

Figure 1:
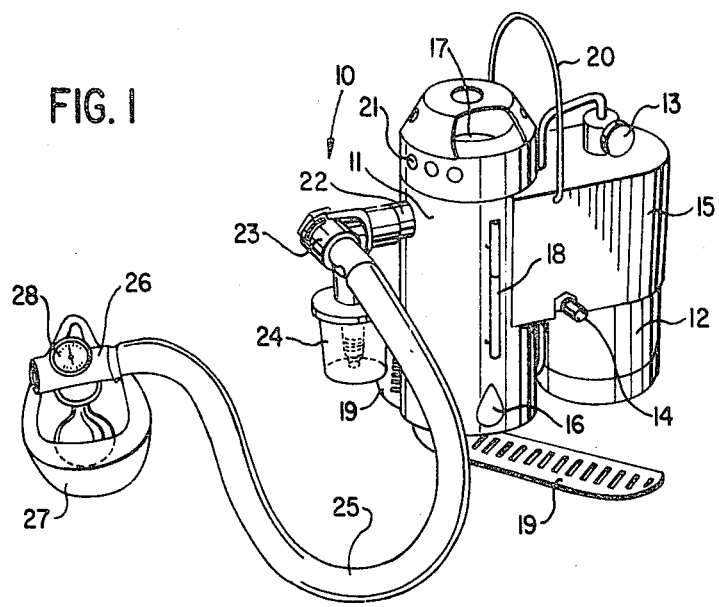
FIG. 1 is a perspective view of one embodiment of an inhalation rewarming apparatus according to this invention.

(i) Description of FIG. 1

As seen in FIG. 1, the inhalation rewarming apparatus 10 includes a steam generator, indicated generally at 11. The steam generator 11 is heated by propane from an adjacent cylinder 12 via shutoff 13 and fine-control valves 14. Heat given off by the generator is directed around the propane tank 12 by a shroud 15 to ensure vaporization of the propane in extremely cold environments. An opening 16 is provided in the generator for lighting the burner. Another opening 17 is provided for adding water to the generator 11. A transparent gauge 18 is provided for indicating water level. Two adjustable stabilizers 19, and a folding carrying handle 20 are also provided.

Steam generated within the steam generator 11 is mixed with ambient air at ambient pressure admitted through apertures 21 and the steam-air mixture is withdrawn at ambient pressure through outlet conduit 22, which leads to a temperature-regulating valve 23. The air-steam mixture is here converted to temperature-controlled, water-saturated air, which leads past a water trap 24 for condensed vapour by a flexible hose 25 to a T-tube 26 attached to a breathing mask 27. T-tube 26 has a flapper valve (not shown) at each end to establish directed water-saturated air flow to and from a patient without significant rebreathing. Temperature of the water-saturated air breathed by the patient is monitored by a dial thermometer 28.

Figure 2:
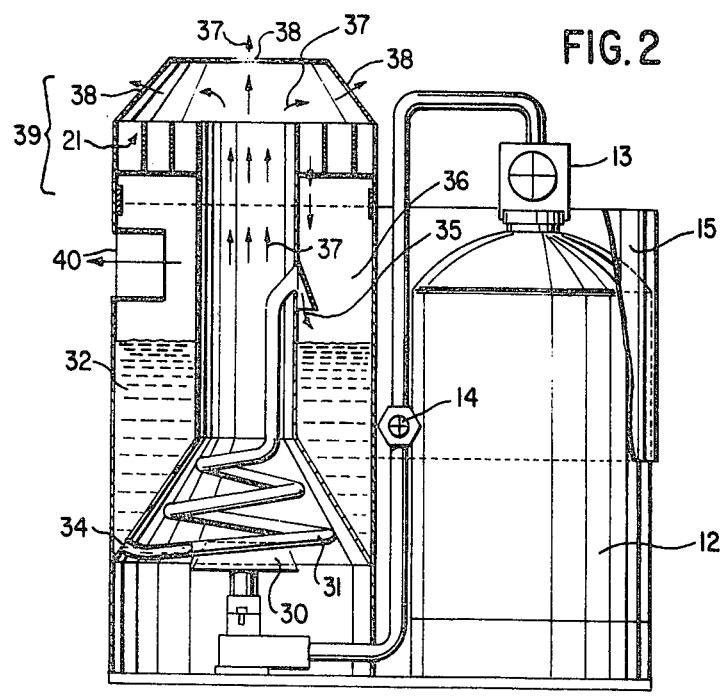
FIG. 2 is a schematic vertical section of one variant of a steam generator forming a part of the inhalation rewarming apparatus according to this invention.

(ii) Description of FIG. 2

One variant of a steam generator 11 is shown in FIG. 2. Propane from a disposable tank 12 is provided to the burner 30 under control by the shutoff valve 13 and the fine-control valve 14. The flame from the burner is applied both to a water-filled coil 31, and to the inner walls of the annular water reservoir 32. The coil 31 leads from the bottom 34 of the water reservoir 32 to the bottom 35 of a steam chamber 36. The exhaust (arrows 37) rises to exit via ports 38 in the generator lid 39. The heat applied to the water-filled coil rapidly produces steam (e.g., in less than 10 seconds) which enters the steam chamber 36. The steam now available in the steam chamber 36 can be drawn (at ambient pressure) through exit 40 to the temperature-regulating valve 23. This causes entry of ambient air (at ambient pressure) at three intake ports 21 in the lid. The route for the air to enter the steam chamber is via circular channels in the lid 39 as indicated by arrows 41. This results in preheating of entering air due to the high temperature of the lid 39 which is heated by the exhaust gases 37. This maintains the high temperature of the air-steam mixture despite cold ambient air supply.

Figure 3:
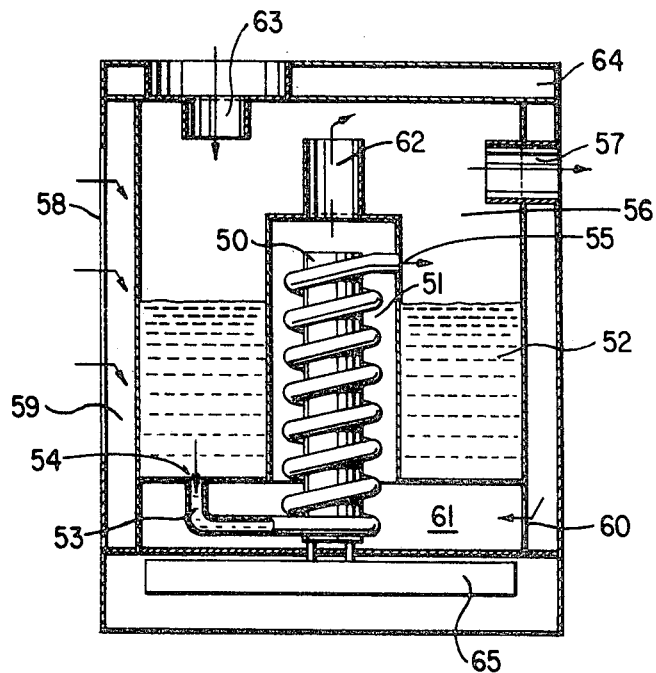
FIG. 3 is a schematic vertical section of another variant of a steam generator forming a part of the inhalation rewarming apparatus according to this invention.

(iii) Description of FIG. 3

Another variant of a steam generator 11 is shown in FIG. 3. The steam generator includes a cylindrical heating element 50 providing a hollow cylindrical heating chamber 51 within an annular water reservoir 52 therearound. A coil 53 connects from the bottom 54 of the water reservoir, around the heating element 50 and to the bottom 55 of the steam chamber 56. This steam thus exits the coil 53 at point 55 and accumulates in the steam chamber 56. It is then available for withdrawal (at ambient pressure) to the temperature-regulating valve 23 via exit 57. This causes entry of ambient air (at ambient pressure) at the intake port 58. This ambient air travels in the annular chamber 59 between the inner and outer walls of the steam generator 11 to the opposite side, where it enters (at opening 60) the chamber 60 containing the electric element. This route allows preheating of cold ambient air. Preheating is continued by the further passage of this air over the electric heating element 50 and coil 53 before it enters the steam chamber 56 via connecting chamber 62. An opening chamber 63 for filling the generator with water is provided in the top 64 of the generator.

The power consumption of the electric element is 250 W at 110 V, which also permits operation from a battery via an inverter. For this reason, a timing circuit (printed circuit board, 65) is provided to obtain a 60/40 on/off duty cycle, thereby extending battery operation without loss of steam production capacity. In this electrical heater system for the generation of steam, it is preferred to use pulsed power of higher wattage so that there is a saving of 40% of electric power over the use of a continuous supply at 60% power. The control circuit is preferably designed for application of full-time 250 watts during warmup. Once this has occurred, the circuit is switched to the more economical 60/40 mode, especially if the ambient temperatures are not too cold.

Figure 4:
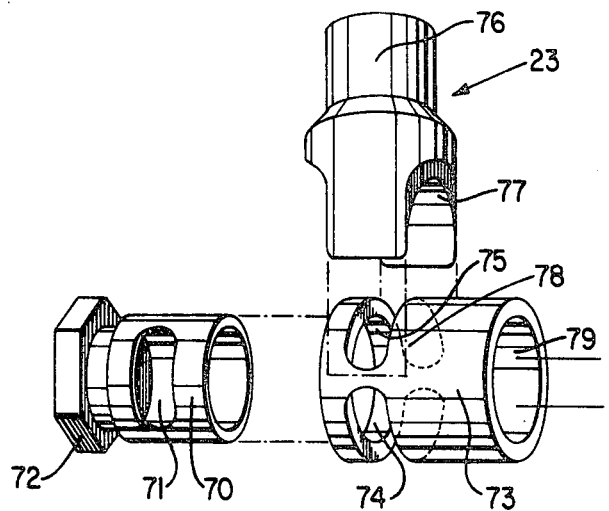
FIG. 4 is an exploded perspective view of a temperature-regulating valve for use in the inhalation rewarming apparatus according to this invention.

(iv) Description of FIG. 4

The structure of a suitable temperature control valve 23 is shown in FIG. 4. The valve 23 includes an inner body 70 in the form of a hollow tube having an arcuate opening 71 therein and closed by a cap 72, and an outer body 73 in the form of an open-ended hollow tube, having a pair of discontinuous arcuate orifices 74, 75 therein. A connecting tube 76 includes a lower saddle connection 77 to the upper portion 78 of the outer body 73. With the air-steam mixture available via connecting tube 76 to arcuate orifice 75, and ambient air via arcuate opening 71 to orifice 74, manual rotation of the inner control body 70, by cap 72 positioned within the outer control body 73, permits selection via orifice 71 of varying inputs of ambient air (to arcuate orifice 74) and the air-steam mixture (to arcuate orifice 75) in proportions to result in temperature control (e.g., 42°–45° C.) of the effluent, water-saturated air leaving the valve at opening 79. A constant flow potential is provided by this valve for all possible control positions.

Figure 5:
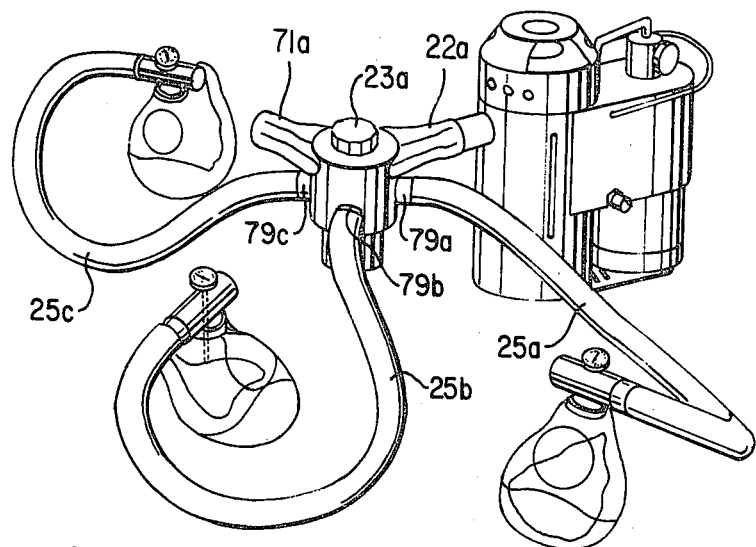
FIG. 5 is a perspective view of a multiple victim inhalation rewarming apparatus according to another embodiment of this invention.

(v) Description of FIG. 5

The multiple patient inhalation rewarming apparatus of FIG. 5 is similar to that shown in FIG. 1 and so the same reference numerals are used for similar parts. The only change is that the temperature control valve 23a is based on a vertical orientation with three control orifices (not shown) between inner and outer tubular bodies, and three outlets 79a, 79b and 79c leading to three flexible conduits 25a, 25b and 25c respectively. An air-steam mixture is conducted through line 22a to valve 23a and an ambient air inlet 71a is provided to the valve 23a.

Figure 6:
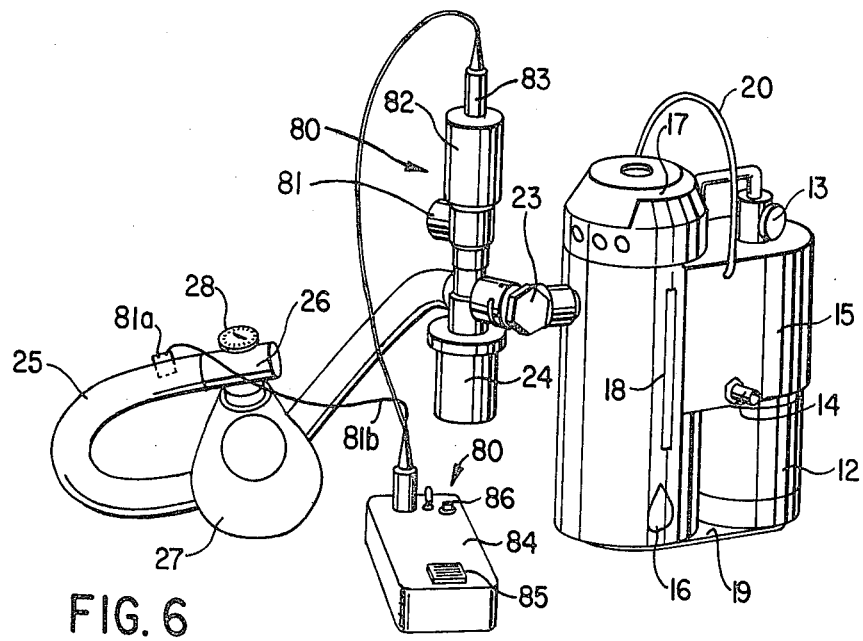
FIG. 6 is a perspective view of an inhalation rewarming apparatus according to yet another embodiment of this invention showing an electronic valve auxiliary temperature control.

(vi) Description of FIG. 6

The apparatus shown in FIG. 6 is similar to that shown in FIG. 1, and so the same reference numerals are used for similar parts. While the temperature-regulating valve 23 is designed for simple and effective operation, there is the possibility of operator failure resulting in excessive temperature of the inhalate water-saturated air. As a safety accessory, an electronic control system 80 can be installed adjacent to the manual valve and operated as a high temperature alarm and limiting device. It is shown in FIG. 6 and its operation is as follows: An electronic temperature sensor 81a is located in the flexible hose 25 near the T-tube 26 and is connected to box 84 via line 81b. When the temperature exceeds 45° C. (or a setting near this according to choice), the orifice 81 allows cool ambient air into the air passage. This opening is provided by a solenoid valve 82 activated via a removable connector 83 from the battery-operated control box 84. During activation of this limiting device, an audible alarm 85 signals the need for manual adjustment of the temperature-regulating valve 23. If such adjustment is not made, the electronic control system 80 will provide control of inhalate temperature within a satisfactory range by intermittent activation. Button 86 permits pre-testing of the function of this accessory device.

Operation of Preferred Embodiments

In operation, the temperature-regulated, water-saturated air from valve 23 is blocked and cooler ambient air is provided for inhalation.

As a general feature of all variants of this invention, it is noted that as long as the saturated air is below 100° C., the introduction of ambient air at the valve desaturates it. Once the saturated air reaches 100° C., it becomes an air/steam mixture. Introduction of ambient air to reduce the temperature of the air/steam mixture plus ambient air combination produces a water-saturated air output once sufficient steam is present in the air/steam mixture.

The carrying out of inhalation rewarming with water-saturated air at a temperature of up to 45° C. has a maximum heating capacity without risking damage to the lungs. This is because of the high heating capacity of water vapour. It is therefore desirable to ensure that the inhaled air is saturated as well as being maintained at a controlled temperature. This is obtained by mixing ambient air with an air-steam mixture that contains sufficient steam to maintain saturation after mixing. In addition, the provision of an air-steam mixture at ambient (i.e., about one atmosphere) pressure enables the patient himself to provide the motive force for inhalation rewarming.

Summary

From the foregoing description, one skilled in the art can easily ascertain the essential characteristics of this invention, and without departing from the spirit and scope thereof, can make various changes and modifications of the invention to adapt it to various usages and conditions. Consequently, such changes and modifications are properly, equitably, and "intended" to be, within the full range of equivalence of the following claims.

I claim:

1. Apparatus for inhalation rewarming for the treatment of victims of hypothermia, comprising:
    (a) a water reservoir;
    (b) a steam chamber communicating with said water reservoir;
    (c) a heater means, associated with said water chamber, for the generation of steam into said steam chamber;
    (d) means for admitting air to said steam chamber, thereby to provide an air-steam mixture;
    (e) first conductor means having inlet means connected to said steam chamber for the conducting of said air-steam mixture from said steam chamber in a first direction and having outlet means;
    (f) valve means in said first conductor means communicating with ambient air for varying the inflow of said ambient air into said conductor means while simultaneously reciprocally varying the inflow of said air-steam mixture from said steam chamber into said conductor means and providing a substantially constant volume flow from said first conductor means, said valve means including actuated operator means for initially introducing sufficient ambient air into said air-steam mixture in said first conductor means to provide a constant volume flow of water-saturated air at a temperature of about 35° C.–about 45° C. and for maintaining said constant volume flow of said water-saturated air at said temperature of about 35° C.–about 45° C.;
    (g) flexible conduit means connected to said outlet means of said first conductor means leading from said valve means for conducting said water-saturated air in said first direction; and
    (h) a breathing mask connected to said flexible conduit means downstream of said valve means, said breathing mask including one-way valves therein to permit said water-saturated air to flow only in said first direction to said breathing mask, whereby said water-saturated air at said temperature of about 35° C.–about 45° C. is drawn into said breathing mask by the negative pressure produced by human inhalation, and exhaled air produced by human inhalation is vented.

2. The apparatus of claim 1 wherein said temperature is about 42°–about 45° C.

3. The apparatus of claim 1 wherein said heater means comprises a propane gas-heated hollow core surrounded by an annular water reservoir.

4. The apparatus of claim 4 including a coil traversing said heated hollow core and leading from the bottom of said water reservoir to the bottom of said steam chamber, whereby water is converted to steam via said water-filled coil.

5. The apparatus of claim 4 wherein said steam chamber is disposed atop said annular water reservoir in open communication therewith.

6. The apparatus of claim 1 wherein said heater means comprises an electrically heated hollow cylinder surrounded by an annular water reservoir.

7. The apparatus of claim 6 including means for preheating said air entering said steam chamber by electric heat from said heater means.

8. The apparatus of claim 6 including a coil traversing said heated hollow cylinder and leading from the bottom of said water reservoir to the bottom of said steam chamber, whereby water is converted to steam via said water-filled coil.

9. The apparatus of claim 8 wherein said steam chamber is disposed atop said annular water reservoir in open communication therewith.

10. The apparatus of claim 1 including means for preheating said air entering said steam chamber by exhaust heat from said heater means.

11. The apparatus of claim 1 wherein said operator means is manually actuated.

12. The apparatus of claim 1 wherein said first conductor means includes a plurality of outlet means leading to a similar plurality of second flexible conduit means, each leading to an associated breathing mask.

13. The apparatus of claim 1 wherein said operator means includes a control means to limit the maximum temperature of said water-saturated air, said control means comprising sensing means, adjacent to said breathing mask, to sense a predetermined maximum temperature of said water-saturated air, and non-manual valve operator means, actuated by said sensing means, to increase the input of ambient air to said valve means, while simultaneously reciprocally reducing the input of said air-steam mixture until the maximum temperature of said water-saturated air is reduced while the volume of flow of said water-saturated air is maintained.

14. The apparatus of claim 1, wherein said first conductor means having said valve means comprises:
(a) a hollow, tubular inner body having a closed end and an opposite open end and an axial flow passage and a single arcuate opening extending through the sidewall thereof;
(b) an outer coaxial, open-ended, hollow tubular body having an axial flow passage and a pair of discontinuous arcuate orifices extending through the sidewall thereof and in alignment with said arcuate opening in said inner body, said outer tubular body being disposed concentrically and relatively rotatably around said inner body;
(c) a hollow connecting tube connected at right angles to one of said discontinuous arcuate openings in said outer body, said connecting tube having an axial flow passage;
(d) said one discontinuous arcuate opening in alignment with said arcuate opening in said inner body defining said inlet means for an air-steam mixture to said valve means through said connecting tube and into said one said discontinuous arcuate orifice;
(e) said valve means communicating with ambient air through said arcuate opening in said hollow inner body in alignment with the other one of said discontinuous arcuate orifices;
(g) said opposite open end of said inner body defining said outlet means connected to said flexible conduit; and means for rotating the inner tubular body with respect to said outer tubular body to change the overlapping areas of said arcuate opening in said inner tubular body and said arcuate openings in said outer tubular body, thereby to allow a varying input of said ambient air and a reciprocal varying input of said air-steam mixture in proportions to result in temperature control of the effluent, water-saturated air while maintaining a constant flow of said water-saturated air.

15. The apparatus of claim 1, wherein said first conductor means having said valve means comprises:
(i) an inner tubular hollow body member having an axial flow passage, and a control orifice in a sidewall thereof;
(ii) an outer tubular hollow body member having an axial flow passage disposed concentrically and in a vertical orientation relatively rotatable to said inner body member, said outer body member having a plurality of orifices in alignment with said control orifice, said flexible conduit means being connected to said outer body member and communicating with said flow passage of said inner hollow body member;
(iii) one of said plurality of orifices in said outer body member in alignment with said control orifice defining an inlet for an air-steam mixture to enter said inner body member;
(iv) another of said plurality of orifices in said outer body member in alignment with said control orifice defining an ambient air inlet means to said inner body member; and
(v) means for rotating the inner tubular body with respect to said outer tubular body to change the overlapping areas of said arcuate opening in said inner tubular body and said arcuate openings in said outer tubular body, thereby to allow a varying input of said ambient air and a reciprocal varying input of said air-steam mixture in proportions to result in temperature control of the effluent, water-saturated air, while maintaining a constant flow of said water-saturated air.

16. The apparatus of claim 1 wherein
said first conductor means includes an outlet port leading from said valve means, a water trap connected to said outlet port for collecting water condensed out of said air-steam mixture in providing said water-saturated air at said temperature of about 35° C.–about 45° C.

17. Apparatus for inhalation rewarming for the treatment of victims of hypothermia, comprising:
(a) a water reservoir;
(b) a steam chamber communicating with said water reservoir;
(c) a heater means, associated with said water chamber, for the generation of steam into said steam chamber;

(d) means for admitting air at ambient pressure to said steam chamber, thereby to provide an air-steam mixture;

(e) first conductor means having inlet means connected to said steam chamber for the conducting of said air-steam mixture at ambient pressure from said steam chamber in a first direction and having outlet means;

(f) valve means in said first conductor means communicating with ambient air for varying the inflow of said ambient air into said conductor means while simultaneously reciprocally varying the inflow of said air-steam mixture from said steam chamber into said conductor means and providing a substantially constant volume flow from said first conductor means, said valve means including actuated operator means for initially introducing sufficient ambient air into said air-steam mixture in said first conductor means to provide a constant volume flow of water-saturated air at a temperature of about 35° C.–about 45° C. and for maintaining said constant volume flow of said water-saturated air at said temperature of about 35° C.–about 45° C.;

(g) flexible conduit means connected to said outlet means of said first conductor means leading from said valve means for conducting said water-saturated air in said first direction; and (h) a breathing mask connected to said flexible conduit means downstream of said valve means, said breathing mask including one-way valves therein to permit said water-saturated air to flow only in said first direction to said breathing mask, whereby said water-saturated air at said temperature of about 35° C.–about 45° C. is drawn into said breathing mask by the negative pressure produced by human inhalation, and exhaled air produced by human inhalation is vented.

18. The apparatus of claim 17 including means for preheating said air entering said steam chamber by exhaust heat from said heater means.

19. The apparatus of claim 17, wherein said first conductor means having said valve means comprises:

(a) a hollow, tubular inner body having a closed end and an opposite open end and an axial flow passage and a single arcuate opening extending through the sidewell thereof;

(b) an outer coaxial, open-ended, hollow tubular body having an axial flow passage and a pair of discontinuous arcuate orifices extending through the sidewall thereof and in alignment with said arcuate opening in said inner body, said outer tubular body being disposed concentrically and relatively rotatably around said inner body;

(c) a hollow connecting tube connected at right angles to one of said discontinuous arcuate openings in said outer body, said connecting tube having an axial flow passage;

(d) said one discontinuous arcuate opening in alignment with said arcuate opening in said inner body defining said inlet means for an air-steam mixture to said valve means through said connecting tube and into said one said discontinuous arcuate orifice;

(e) said valve means communicating with ambient air through said arcuate opening in said hollow inner body the other one of said discontinuous arcuate orifices;

(f) said opposite open end of said inner body defining said outlet means connected to said flexible conduit; and (g) means for rotating the inner tubular body with respect to said outer tubular body to change the overlapping areas of said arcuate opening in said inner tubular body and said arcuate openings in said outer tubular body, thereby to allow a varying input of said ambient air and a reciprocal varying input of said air-steam mixture in proportions to result in temperature control of the effluent, water-saturated air while maintaining a constant flow of said water-saturated air.

20. The apparatus of claim 17, wherein said first conductor means having said valve means comprises:

(i) an inner tubular hollow body member having an axial flow passage, and a control orifice in a sidewall thereof;

(ii) an outer tubular hollow body member having an axial flow passage disposed concentrically and in a vertical orientation relatively rotatable to said inner body member, said outer body member having a plurality of orifices in alignment with said control orifice, said flexible conduit means being connected to said outer body member and communicating with said flow passage of said inner hollow body member;

(iii) one of said plurality of orifices in said outer body member in alignment with said control orifice defining an inlet for an air-stream mixture to enter said inner body member;

(iv) another of said plurality of orifices in said outer body member in alignment with said control orifice defining an ambient air inlet means to said inner body member; and (v) means for rotating the inner tubular body with respect to said outer tubular body to change the overlapping areas of said arcuate opening in said inner tubular body and said arcuate openings in said outer tubular body, thereby to allow a varying input of said ambient air and a reciprocal varying input of said air-steam mixture in proportions to result in temperature control of the effluent, water-saturated air, while maintaining a constant flow of said water-saturated air.

21. The apparatus of claim 17 wherein said temperature is about 42° C.–about 45° C.

22. The apparatus of claim 17 wherein said first conductor means includes an outlet port leading from said valve means, a water trap connected to said outlet port for collecting water condensed out of said air-steam mixture in providing said water-saturated air at said temperature of about 35° C.–about 45° C.

23. The apparatus of claim 17 wherein said operator means is manually actuated.

24. Apparatus for inhalation rewarming for the treatment of victims of hypothermia, comprising:

(a) first conductor means having inlet means for connection to a source of an air-steam mixture for conducting said air-steam mixture in a first direction and outlet means;

(b) valve means in said first conductor means communicating with ambient air for varying the inflow of said ambient air into said conductor means while simultaneously reciprocally varying the inflow of said air-steam mixture into said conductor means from a source of air-steam mixture and providing a substantially constant volume flow from said first conductor means, said valve means including actuated operator means for initially introducing sufficient ambient air into said air-steam mixture in said first conductor means to provide a substantially constant volume flow of water-saturated air at a temperature of about 35° C.–about 45° C.;

(c) flexible conduit means connected to said outlet means of said first conductor means leading from said valve means for conducting said water-saturated air in said first direction; and (d) a breathing mask connected to said flexible conduit means downstream of said valve means, said breathing mask including one-way valves therein to permit said water-saturated air to flow only in said first direction to said breathing mask, whereby said water-saturated air at said temperature of about 35° C.–about 45° C. is drawn into said breathing mask by the negative pressure produced by human inhalation, and exhaled air produced by human inhalation is vented.

25. The apparatus of claim 24, wherein said first conductor means having said valve means comprises:

(a) a hollow, tubular inner body having a closed end and an opposite open end and an axial flow passage and a single arcuate opening extending through the sidewall thereof;

(b) an outer coaxial, open-ended, hollow tubular body having an axial flow passage and a pair of discontinuous arcuate orifices extending through the sidewall thereof and in alignment with said arcuate opening in said inner body, said outer tubular body being disposed concentrically and relatively rotatably around said inner body;

(c) a hollow connecting tube connected at right angles to one of said discontinuous arcuate openings in said outer body, said connecting tube having an axial flow passage;

(d) said one discontinuous arcuate opening in alignment with said arcuate opening in said inner body defining said inlet means for an air-steam mixture to said valve means through said connecting tube and into said one said discontinuous arcuate orifices;

(e) said valve means communicating with ambient air through said arcuate opening in said hollow inner body in alignment with the other one of said discontinuous arcuate orifices;

(f) said opposite open end of said inner body defining said outlet means connected to said flexible conduit; and (g) means for rotating the inner tubular body with respect to said outer tubular body to change the overlapping areas of said arcuate opening in said inner tubular body and said arcuate openings in said outer tubular body, thereby to allow a varying input of said ambient air and a reciprocal varying input of said air-steam mixture in proportions to result in temperature control of the effluent, water-saturated air while maintaining a constant flow of said water-saturated air.

26. The apparatus of claim 24 wherein said first conductor means having said valve means comprises:

(i) an inner tubular hollow body member having an axial flow passage, and a control orifice in a sidewall thereof;

(ii) an outer tubular hollow body member having an axial flow passage disposed concentrically and in a vertical orientation relatively rotatable to said inner body member, said outer body member having a plurality of orifices in alignment with said control orifice, said flexible conduit means being connected to said outer body member and communicating with said flow passage of said inner hollow body member;

(iii) one of said plurality of orifices in said outer body member in alignment with said control orifice defining an inlet for an air-steam mixture to enter said inner body member;

(iv) another of said plurality of orifices in said outer body member in alignment with said control orifice defining an ambient air inlet means to said inner body member; and (v) means for rotating the inner tubular body with respect to said outer tubular body to change the overlapping areas of said arcuate opening in said inner tubular body and said arcuate openings in said outer tubular body, thereby to allow a varying input of said ambient air and a reciprocal varying input of said air-steam mixture in proportions to result in temperature control of the effluent, water-saturated air, while maintaining a constant flow of said water-saturated air.

27. The apparatus of claim 24 wherein said first conductor means includes an outlet port leading from said valve means, a water trap connected to said outlet port for collecting water condensed out of said air-steam mixture in providing said water-saturated air at said temperature of about 35° C.–about 45° C.

28. A method for the treatment of a human suffering from hypothermia which comprises the steps of:

(1) generating an air-steam mixture;

(2) converting said air-steam mixture to water-saturated air at a temperature of about 35° C.–about 45° C. by the addition of controlled amounts of ambient air to said air-steam mixture while substantially simultaneously condensing water out of said air-steam mixture;

(3) maintaining a substantially constant volume flow of said water-saturated air at said temperature of about 35° C.–about 45° C. by varying the volume of ambient air while simultaneously reciprocally varying the volume of said air-steam mixture; and (4) arranging for said human to inhale said water-saturated air at said temperature of about 35° C.–about 45° C. by spontaneous ventilation.

* * * * *